(12) United States Patent
Jacobsen et al.

(10) Patent No.: US 7,969,659 B2
(45) Date of Patent: Jun. 28, 2011

(54) GRIN LENS MICROSCOPE SYSTEM

(75) Inventors: Stephen C. Jacobsen, Salt Lake City, UT (US); David P. Marceau, Salt Lake City, UT (US)

(73) Assignee: Sterling LC, Salt Lake City, UT (US)

( * ) Notice: Subject to any disclaimer, the term of this patent is extended or adjusted under 35 U.S.C. 154(b) by 108 days.

(21) Appl. No.: 12/008,486

(22) Filed: Jan. 11, 2008

(65) Prior Publication Data

US 2009/0180197 A1 Jul. 16, 2009

(51) Int. Cl.
    *G02B 3/00* (2006.01)
(52) U.S. Cl. ..................... 359/652; 359/368
(58) Field of Classification Search ............. 359/652, 359/368
    See application file for complete search history.

(56) References Cited

U.S. PATENT DOCUMENTS

| | | |
|---|---|---|
| 3,817,635 A | 6/1974 | Kawahara |
| 3,856,000 A | 12/1974 | Chikama |
| 3,971,065 A | 7/1976 | Bayer |
| 4,283,115 A | 8/1981 | Fraissl |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,622,954 A | 11/1986 | Arakawa et al. |
| 4,646,724 A | 3/1987 | Sato et al. |
| 4,706,118 A | 11/1987 | Kato et al. |
| 4,723,843 A | 2/1988 | Zobel |
| 4,725,721 A | 2/1988 | Nakamura |
| 4,745,470 A | 5/1988 | Yabe et al. |

(Continued)

FOREIGN PATENT DOCUMENTS

CN 1481753 3/2004

(Continued)

OTHER PUBLICATIONS

Nguyen, Clark, "Communications Applications of Microelectromechanical Systems," Proceedings, Sensors Expo, May 19-21, 1998, San Jose, CA. pp. 447-455.

(Continued)

*Primary Examiner* — Joseph Martinez
*Assistant Examiner* — James R Greece
(74) *Attorney, Agent, or Firm* — Thorpe North & Western LLP (57) ABSTRACT

A device for magnifying an object comprising an SSID having at least one imaging array disposed on a distal end thereof. The device further comprises a first optical element disposed on the distal end of the SSID wherein the first optical element has a distal end and a proximal end defining a first longitudinal length. A GRIN lens is disposed on the distal end of the first optical element and a second optical element is disposed on the distal end of the GRIN lens defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end of the first optical element.

15 Claims, 5 Drawing Sheets

U.S. PATENT DOCUMENTS

| | | | |
|---|---|---|---|
| 4,745,471 A | 5/1988 | Takamura et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,926,257 A | 5/1990 | Miyazaki |
| 4,932,394 A | 6/1990 | Nanaumi |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,040,069 A | 8/1991 | Matsumoto et al. |
| 5,061,036 A | 10/1991 | Gordon |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,130,804 A | 7/1992 | Tamura et al. |
| 5,166,656 A | 11/1992 | Badehi et al. |
| 5,191,203 A | 3/1993 | McKinley |
| 5,198,894 A | 3/1993 | Hicks |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,291,010 A | 3/1994 | Tsuji |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 1/1995 | Brown et al. |
| 5,398,685 A | 3/1995 | Wilk et al. |
| 5,402,769 A | 4/1995 | Tsuji |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljic et al. |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna |
| 5,547,906 A | 8/1996 | Badehi |
| 5,594,497 A | 1/1997 | Ahern |
| 5,603,687 A | 2/1997 | Hori et al. |
| 5,630,788 A | 5/1997 | Forkner et al. |
| 5,647,368 A | 7/1997 | Zeng et al. |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,792,984 A | 8/1998 | Bloom |
| 5,800,341 A | 9/1998 | McKenna et al. |
| 5,808,665 A | 9/1998 | Green |
| 5,818,644 A | 10/1998 | Noda |
| 5,827,172 A | 10/1998 | Takahashi et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,998,878 A | 12/1999 | Johnson |
| 5,999,327 A | 12/1999 | Nagaoka |
| 6,008,123 A | 12/1999 | Kook et al. |
| 6,022,758 A | 2/2000 | Badehi |
| 6,040,235 A | 3/2000 | Badehi |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,142,930 A | 11/2000 | Ito et al. |
| 6,161,035 A | 12/2000 | Furusawa |
| 6,184,923 B1 | 2/2001 | Miyazaki |
| 6,211,955 B1 | 4/2001 | Basiji et al. |
| 6,261,226 B1 | 7/2001 | McKenna et al. |
| 6,262,855 B1 | 7/2001 | Greisz |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsue |
| 6,366,726 B1 | 4/2002 | Wach et al. |
| 6,384,397 B1 | 5/2002 | Takiar et al. |
| 6,396,116 B1 | 5/2002 | Kelly et al. |
| 6,456,423 B1 | 9/2002 | Nayfeh et al. |
| 6,485,413 B1 | 11/2002 | Boppart et al. |
| 6,522,913 B2 | 2/2003 | Swanson et al. |
| 6,533,722 B2 | 3/2003 | Nakashima |
| 6,537,205 B1 | 3/2003 | Smith |
| 6,561,972 B2 | 5/2003 | Ooshima et al. |
| 6,595,913 B2 | 7/2003 | Takahashi |
| 6,622,367 B1 | 9/2003 | Bolduc et al. |
| 6,643,071 B2 | 11/2003 | Schnitzer |
| 6,658,279 B2 | 12/2003 | Swanson et al. |
| 6,695,787 B2 | 2/2004 | Hogenkijk et al. |
| 6,719,686 B2 | 4/2004 | Coakley et al. |
| 6,761,684 B1 | 7/2004 | Speier |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,879,851 B2 | 4/2005 | McNamara et al. |
| 6,898,458 B2 | 5/2005 | Zeng et al. |
| 6,900,913 B2 | 5/2005 | Chen |
| 6,937,268 B2 | 8/2005 | Ogawa |
| 6,944,204 B2 | 9/2005 | Zhou et al. |
| 6,953,432 B2 | 10/2005 | Schiefer |
| 6,960,165 B2 | 11/2005 | Ueno et al. |
| 6,982,740 B2 | 1/2006 | Adair et al. |
| 7,030,904 B2 | 4/2006 | Adair et al. |
| 7,033,317 B2 | 4/2006 | Pruitt |
| 7,075,576 B2 | 7/2006 | Creasey et al. |
| 7,091,500 B2 | 8/2006 | Schnitzer |
| 7,098,871 B1 | 8/2006 | Tegreene et al. |

| | | | |
|---|---|---|---|
| 7,153,299 | B1 | 12/2006 | Tu et al. |
| 7,166,537 | B2 | 1/2007 | Jacobsen et al. |
| 7,218,822 | B2 | 5/2007 | Treado et al. |
| 7,221,388 | B2 | 5/2007 | Sudo et al. |
| 7,304,310 | B1 | 12/2007 | Shortt et al. |
| 7,591,780 | B2 * | 9/2009 | Jacobsen et al. ............... 600/109 |
| 7,629,659 | B2 | 12/2009 | Jacobsen et al. |
| 2001/0007051 | A1 | 7/2001 | Nakashima |
| 2001/0007511 | A1 | 7/2001 | Minami et al. |
| 2001/0024848 | A1 | 9/2001 | Nakamura |
| 2001/0049509 | A1 | 12/2001 | Sekine et al. |
| 2002/0007110 | A1 | 1/2002 | Irion |
| 2002/0080248 | A1 | 6/2002 | Adair et al. |
| 2002/0111534 | A1 | 8/2002 | Suzuki et al. |
| 2002/0166946 | A1 | 11/2002 | Iizuka et al. |
| 2002/0188204 | A1 | 12/2002 | McNamara |
| 2002/0193660 | A1 | 12/2002 | Weber |
| 2003/0071342 | A1 | 4/2003 | Honda et al. |
| 2003/0092995 | A1 | 5/2003 | Thompson |
| 2003/0220574 | A1 * | 11/2003 | Markus et al. ................ 600/466 |
| 2003/0222325 | A1 * | 12/2003 | Jacobsen et al. ............. 257/432 |
| 2004/0017961 | A1 | 1/2004 | Petersen et al. |
| 2004/0059204 | A1 | 3/2004 | Marshall |
| 2004/0097804 | A1 | 5/2004 | Sobe |
| 2004/0181148 | A1 | 9/2004 | Uchiyama et al. |
| 2004/0225222 | A1 | 11/2004 | Zeng et al. |
| 2005/0054902 | A1 | 3/2005 | Konno |
| 2005/0154277 | A1 | 7/2005 | Tang et al. |
| 2005/0174649 | A1 | 8/2005 | Okada et al. |
| 2005/0231718 | A1 | 10/2005 | Goodall et al. |
| 2005/0234345 | A1 | 10/2005 | Yang |
| 2005/0267340 | A1 | 12/2005 | Ishihara et al. |
| 2005/0288555 | A1 | 12/2005 | Binmoeller |
| 2006/0069312 | A1 | 3/2006 | O'Connor |
| 2006/0146172 | A1 | 7/2006 | Jacobsen et al. |
| 2008/0045794 | A1 | 2/2008 | Belson |

FOREIGN PATENT DOCUMENTS

| | | |
|---|---|---|
| EP | 0482997 | 10/1991 |
| EP | 0639043 | 2/1995 |
| EP | 0681809 | 11/1995 |
| EP | 1104182 | 5/2001 |
| EP | 1477104 | 11/2004 |
| EP | 1626436 | 2/2006 |
| JP | 63-155115 | 6/1988 |
| JP | 5-049602 | 3/1993 |
| JP | 58-046924 | 3/1993 |
| JP | 2005334462 | 12/2005 |
| JP | 2006-162418 | 6/2006 |
| JP | 2007/312290 | 11/2007 |
| WO | WO98/38907 | 9/1998 |
| WO | WO99/40624 | 8/1999 |
| WO | WO00/54033 | 9/2000 |
| WO | WO 03/081831 | 10/2003 |
| WO | WO2006/060777 | 6/2006 |

OTHER PUBLICATIONS

Fujimoto, JG et al., "High resolution in vivo intra-arterial imaging with optical coherence tomography," Heart, 1999, vol. 82, pp. 128-133.
Boppart, S.A. et al., "Forward-imaging instruments for optical coherence tomography." Optics Letters, Nov. 1, 1997, vol. 22, No. 21, pp. 1618-1620.
Tearney, G.J. et al., "Scanning single-mode fiber optic catheter-endoscope for otpical coherence tomography," Optics Letters, Apr. 1, 1996, vol. 21, No. 7, pp. 543-545.
Boppart, S.A. et al., "Optical imaging technology in minimally invasive surgery," Surg. Endosc., 1999, vol. 13, pp. 718-722.
Zeis, Michael et al., "Color Business Report," ISSN 1055-3339. Jul. 2002, p. 5.
Microcam, Minast Project 5.04, Nov. 11, 1999, http://www.imt.unine.ch/ESPLAB/www/projects/Microcam/, pp. 1-16.
Literature from GRIN TECH, "In vivo medical confocal imaging and optical coherence tomography," www.grintech.de, Revision Jun. 2001, pp. 1-3.
Jacobsen, Stephen C., U.S. Appl. No. 10/391,489, filed Mar. 17, 2003.
Jacobsen, Stephen C., U.S. Appl. No. 10/391,490, filed Mar. 17, 2003.
Jacobsen, Stephen C., U.S. Appl. No. 10/391,513, filed Mar. 17, 2003.
Jacobsen, Stephen C., U.S. Appl. No. 11/292,902, filed Dec. 1, 2005.
Jacobsen, Stephen C., U.S. Appl. No. 12/079,741, filed Mar. 27, 2008.
Jacobsen, Stephen C., U.S. Appl. No. 11/810,702, filed Jun. 5, 2007.
Jacobsen, Stephen C., U.S. Appl. No. 12/152,730, filed May 16, 2008.
Jacobsen, Stephen C., U.S. Appl. No. 12/487,495, filed Jun. 18, 2009.
Jacobsen, Stephen C., U.S. Appl. No. 12/487,481, filed Jun. 18, 2009.
Jacobsen, Stephen C., U.S. Appl. No. 12/512,188, filed Jul. 30, 2009.
Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.
J. Knittel et al., "Endoscope-compatible confocal microscope using a gradient index-lens system" Optics Communications, vol. 188, Issue 5-6, Feb. 2001, pp. 267-273.
http://news.thomasnet.com/fullstory/23462 "Near-IR Camera Utilizes CCD Array with Phosphor Coating"; Jun. 11, 2003; 5 pages.
Jacobsen, Stephen C.; U.S. Appl. No. 12/611,776; filed Nov. 3, 2009.
Jacobsen, Stephen C.; U.S. Appl. No. 12/792,562; filed Jun. 2, 2010.
Jacobsen, Stephen C.; U.S. Appl. No. 12/896,731; filed Oct. 1, 2010.
Jacobsen, Stephen C.; U.S. Appl. No. 12/896,732; filed Oct. 1, 2010.
Jacobsen, Stephen C.; U.S. Appl. No. 12/896,737; filed Oct. 1, 2010.
Jacobsen, Stephen C.; U.S. Appl. No. 12/896,743; filed Oct. 1, 2010.
Jacobsen, Stephen C.; U.S. Appl. No. 12/938,672; filed Nov. 3, 2010.
Jacobsen, Stephen C.; U.S. Appl. No. 12/946,442; filed Nov. 15, 2010.
Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.

* cited by examiner

GRIN LENS MICROSCOPE SYSTEM

BACKGROUND

The present invention relates generally to miniature microscope system. More particularly, the present invention relates to GRIN ("graded index") lens microscope system which allows for magnification of an object in a video microscope system without the large cumbersome impairments of existing video microscope systems.

An important tool for research as well as diagnosis of medical problems is the optical microscope. A conventional optical microscope includes an objective lens and an imaging lens. Exemplary microscopes include objective and imaging lenses that are compound lenses or lens systems. Both objective and imaging lenses contribute to image magnification. The objective lens forms a first magnified image of an object being examined. The first image becomes the object for the imaging lens which produces a further magnified final image. The total magnification is the product of the separate magnifications produced by the objective lens and the imaging lens. The two lenses are utilized to reduce optical aberrations, particularly chromatic aberrations and spherical aberrations. Chromatic aberration is the phenomenon of different colors focusing at different distances from a lens which produces soft overall images, and color fringing at high-contrast edges, like an edge between black and white. Use of an optical microscope to examine internal tissues of a large animal typically entails removing the tissues from the animal. The removal facilitates positioning the microscopes objective lens for viewing the tissues.

To record or photograph images from an optical microscope, a digital camera may be optically and mechanically adapted to the microscope. An adapter connects the camera with the microscope. A firm mechanical connection is particularly important, because even the smallest movements (vibrations) of the camera strongly reduce the image quality. Furthermore, the light path must be optically adapted so that a fully lit, focused image is projected to the camera sensor (CCD/CMOS). There are several methods for attaching a digital camera to a microscope. One solution is to use the phototube. Using the adapter, the digital camera is screwed firmly onto the tube. The two oculars continue to be used for the visual observation of the specimen. Unfortunately, almost all microscopes that are equipped with a phototube are very costly. Another option is to directly place a digital camera, without any adaptations, directly to the ocular, and to capture an image with a steady hand. Due to the lack of optical adaptation, however, this method produces a smaller, vignetted image in most cases wherein the edges of an image are darker than the center. This effect causes only a small part of the sensor to be optimally used; the rest remains black. A more professional, but also more costly solution is to use a tube adapter. With this method, the ocular is removed and an adapter is fitted into the phototube with the digital camera. The adapter acts as a mechanical and optical interface between microscope and digital camera. This makes it possible to avoid motion blurs due to camera shake and vignettation effects, leading to a much higher quality of the image.

SUMMARY OF THE INVENTION

It has been recognized that it would be advantageous to develop a robust, simple-to-use, miniature microscope system suitable for use as a self-contained portable video system which may be used for in-vivo examination, photography, and video recording of tissues.

The invention provides a device for magnifying an object comprising an SSID having at least one imaging array disposed on a distal end thereof. The device further comprises a first optical element disposed on the distal end of the SSID wherein the first optical element has a distal end and a proximal end defining a first longitudinal length. A GRIN lens is disposed on the distal end of the first optical element and a second optical element is disposed on the distal end of the GRIN lens defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end of the first optical element.

In one embodiment of the present invention an outer surface of the (i) first optical element, (ii) the GRIN lens, and (iii) at least a portion of the second optical element are coated with an opaque material. Further, a light source can be disposed exterior to the first and second optical elements and the GRIN lens, capable of propagating light at a predetermined wavelength.

In another embodiment of the present invention a light collimation device is disposed on a distal end of the second optical element. In yet another embodiment, a light reflection device is disposed on a distal end of the second optical element such as an annular prism.

In another embodiment of the present invention, the device further comprises an SSID with a plurality of imaging arrays disposed thereon wherein each imaging array has an image magnification system disposed thereon. The image magnification system comprises a first optical element disposed on a distal end of the imaging array and has a distal end and a proximal end defining a first longitudinal length. The image magnification system further comprises a GRIN lens disposed on the distal end of the first optical element and a second optical element disposed on the distal end of the GRIN lens defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end of the first optical element.

In one embodiment of the present invention, the first optical element and/or the second optical element comprise a transparent cylinder. In one aspect, the first and/or second optical elements can comprise a solid silica-based material. In yet another aspect, the first and/or second optical elements comprise a fluid filled cylinder having an index of refraction less than 1.1.

In another embodiment of the present invention, a SSID microscope is provided comprising an SSID having at least one imaging array disposed thereon and a longitudinally adjustable first optical element having a distal end and a proximal end disposed on a distal end of the SSID. The microscope further comprises a GRIN lens disposed on the distal end of the first optical element having a distal end and a proximal end defined by a fixed longitudinal length and a longitudinally adjustable second optical element disposed on the distal end of the GRIN lens. The ratio of the longitudinal length of the first optical element to the longitudinal length of the second optical element is maintained such that when viewing the object at a predetermined wavelength of light, the object is magnified at a predetermined level of magnification and the focal plane of the magnified object is aligned at the proximal end of the first optical element.

In one embodiment of the present invention, the first and/or second optical elements comprise an adjustable volume of air. In one aspect, the outer perimeter of the first and/or second optical elements is defined by a cylindrical member.

The present invention further comprises a method of magnifying an objection comprising the steps of (i) providing a device having an SSID and first and second optical elements with a GRIN lens disposed between the first and second optical elements wherein the ratio of the longitudinal length of the first optical element to the second optical element is maintained such that when viewing the object at a predetermined wavelength of light, the object is magnified at a predetermined level of magnification and the focal plane of the magnified object is aligned at the proximal end of the first optical element, (ii) orienting the device such that the object is disposed adjacent the distal end of the second optical element, (iii) propagating a predetermined wavelength of light onto the surface of said object, and (iv) receiving a portion of the propagated light onto the SSID.

In yet another embodiment of the present invention, a method of magnifying an object is disclosed, comprising the steps of (i) providing a device having an SSID and first and second optical elements with a GRIN lens disposed between the first and second optical elements wherein the ratio of the longitudinal length of the first optical element to the second optical element is maintained such that when viewing the object at a predetermined wavelength of light, the object is magnified at a predetermined level of magnification and the focal plane of the magnified object is aligned at the proximal end of the first optical element, (ii) orienting the device such that the object is disposed adjacent the distal end of the second optical element, (iii) propagating a predetermined wavelength of light into the surface of said object, and (iv) receiving a portion of the propagated light onto the SSID.

In another embodiment of the invention, the method of magnifying an object further comprises the step of generating a signal in response to the light received by the SSID and transmitting said signal to a signal processor and image display.

In yet another embodiment of the present invention, the method of magnifying an object further comprises the step of adjusting the longitudinal length of the first optical element and the second optical element to adjust the magnification of the object. In another embodiment of the present invention, the method of magnifying an object further comprises the step of placing the distal end of the second optical element directly on the object to be magnified.

In one embodiment of the present invention, the method of magnifying an object further comprises the step of adjusting the longitudinal lengths of the first and second optical elements and changing the wavelength of light propagated into or onto the object.

In additional embodiment of the present invention a device for magnifying an object is disclosed comprising an SSID having at least one imaging array disposed on a distal end thereof. A first optical element is disposed on the distal end of the SSID, the first optical element having a distal end and a proximal end defining a first longitudinal length. A second optical element is disposed on the distal end of the first optical element defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end of the first optical element. In one aspect of the present invention, the first optical element is a GRIN lens.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 3b is a perspective view of the SSID microscope of FIG. 3a;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," or "SSID chip" in the exemplary embodiments generally comprises an imaging array or pixel array for gathering image data. In one embodiment, the SSID can comprise a silicon or silicon-like substrate or amorphous silicon thin film transistors (TFT) having features typically manufactured therein. Features can include the imaging array, conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, radiation emitting devices, and laser diodes, for example.

"GRIN lens" or "graduated refractive index lens" refers to a specialized lens that has a refractive index that is varied radially from a center optical axis to the outer diameter of the lens.

In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens.

With these definitions in mind, reference will now be made to the accompanying drawings, which illustrate, by way of example, embodiments of the invention.

Figure 1A:
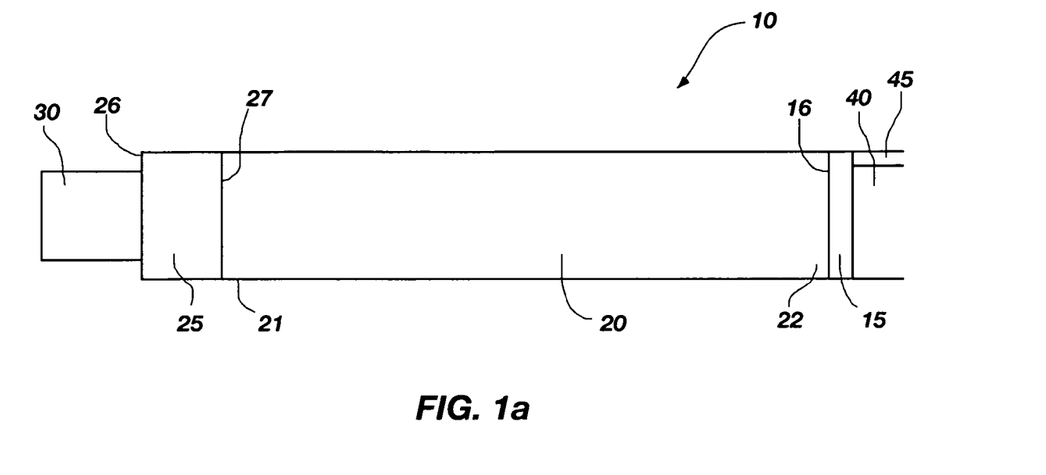
FIG. 1a is a side view of a SSID microscope in accordance with an embodiment of the present invention.
Figure 1B:
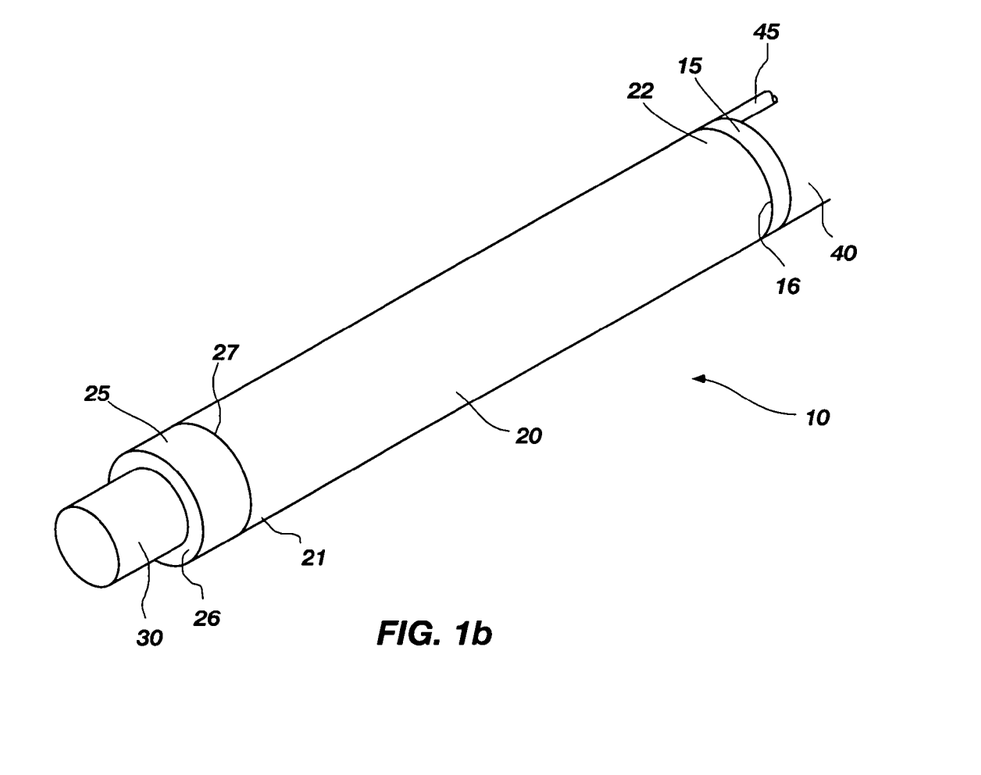
FIG. 1b is a perspective view of the SSID microscope of FIG. 1.

Use of miniature imaging systems in connection with medical imaging has been disclosed in U.S. patent application Ser. No. 10/391,490 which is incorporated herein by reference in its entirety. At times, it may be desirable to magnify the image being observed by the miniature imaging system. As illustrated in FIGS. 1a and 1b, the present invention provides a miniature device, shown generally at 10, for magnifying an object. The device comprises an SSID 15 having at least one imaging array disposed on a distal end 16 thereof and a first optical element 20 disposed on the distal end 16 of the SSID 15. The first optical element 20 has a distal end 21 and a proximal end 22 defining a first longitudinal length. A GRIN lens 25 is disposed on the distal end 21 of the first optical element 20 and a second optical element 30 is disposed on the distal end 26 of the GRIN lens 25 defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end 22 of the first optical element 20.

In one embodiment, the device for magnifying an object is disposed on a distal end of a catheter 40. The SSID 15 is operatively coupled to an umbilical 45 which may serve as an electrical connection for providing energy to the SSID and also as a data transmission conduit. In one embodiment, the umbilical 45 is connected to a data processor and display device (not shown). In another embodiment, the umbilical 45 is utilized to transmit light to the microscope device.

Figure 2:
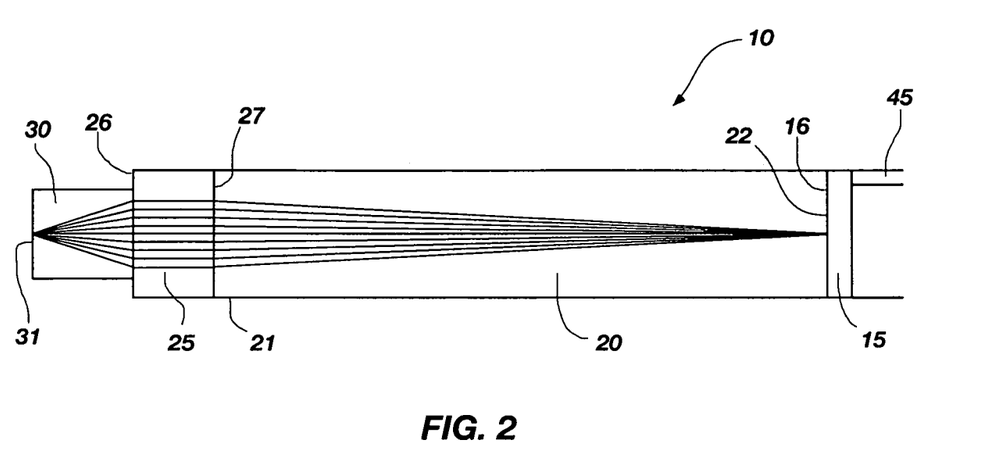
FIG. 2 is a side view of the SSID microscope of FIG. 1 illustrating one example of light travel within the microscope.

With reference to FIG. 2, the object plane of the microscope 10 is oriented at the distal end 31 of the second optical element 30 and the image plane of the microscope 10 is oriented at the proximal end 22 of the first optical element. The microscope 10 thus will form a magnified image on the SSID 15 of an object that is in contact with or in the object plane. The optical magnification of the microscope 10 is governed by equation 1 below:

$$M = \frac{l_1}{l_2} \quad (1)$$

Where M is the magnitude of the magnification of the object in the object plane, $l_1$ is the longitudinal length of the first optical element 20, and $l_2$ is the longitudinal length of the second optical element 30.

Different wavelengths of light refracted by a lens focus at different points away from the lens. This phenomena is sometimes referred to as chromatic aberration. Accordingly, different wavelengths of light propagated through a GRIN lens will have different focal points. FIG. 2 illustrates one example whereby the ratio of longitudinal length of the first optical element to the second optical element results in a predetermined level of magnification. The distance of the proximal end 22 of the first optical element 20 to the proximal end 27 of the GRIN lens 25 (i.e., the first longitudinal length referenced above) is maintained such that the focal length for a predetermined wavelength of light is approximately equal to the first longitudinal length. Thus, for a predetermined wavelength of light, the focal plane is positioned at approximately the proximal end of the first optical element 20 (i.e., approximately on the face of the SSID 15). For example, for a SSID microscope 10 having a first optical element 20 having a longitudinal length of three millimeters (3 mm) and a second optical element 30 having a longitudinal length of one millimeter (1 mm), the focal plane of the object would align itself at the proximal end 22 of the first optical element 20 (in other words, on the face of the SSID) when light at the designed wavelength(s) is propagated onto or through the object and is reflected back through the microscope 10. The resulting level of magnification of the object in this example would be three times the unaided optical magnification.

In one exemplary embodiment, the microscope 10 would have a maximum diameter of approximately six hundred microns (0.6 mm). Advantageously, a user of the microscope, such as a medical practitioner, can advance the microscope into portions of the body and conduct an in-vivo examination of bodily tissues.

Figure 3A:
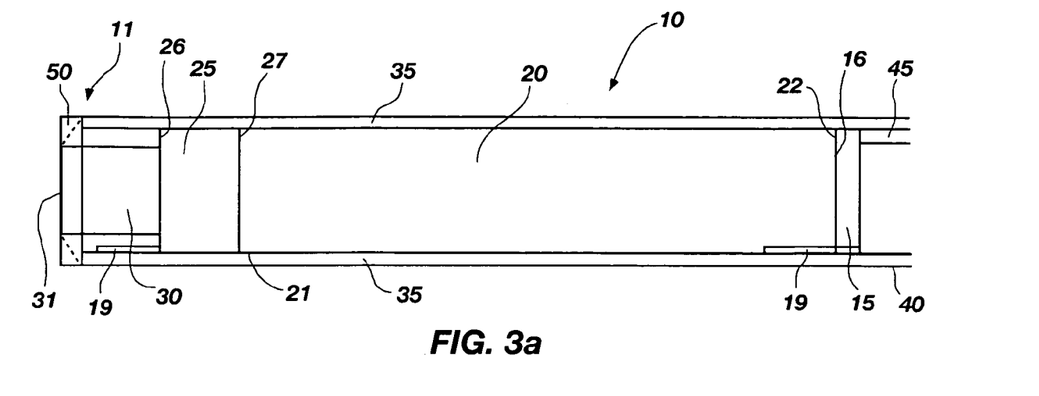
FIG. 3a is a side view of a SSID microscope in accordance with one embodiment of the present invention.
Figure 3B:
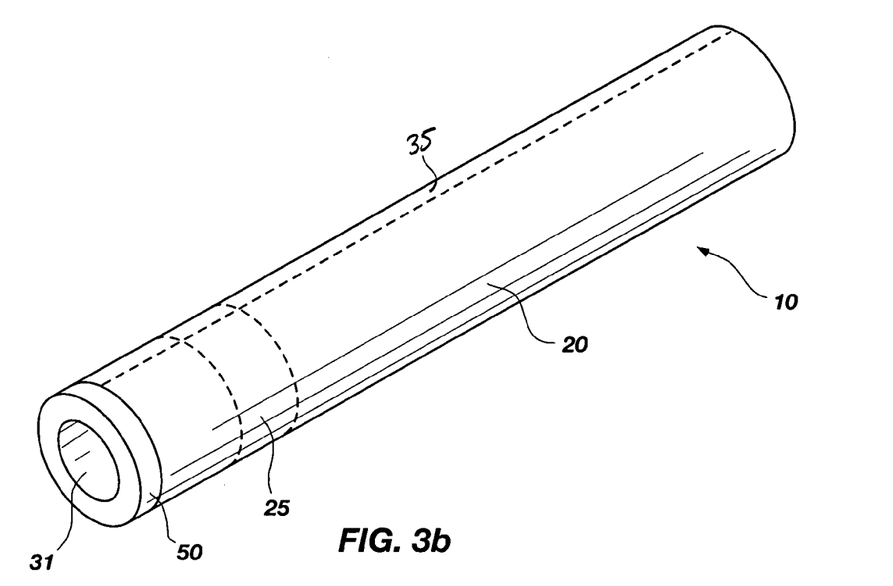

Referring now to FIGS. 3a and 3b, in one embodiment of the present invention, an SSID microscope is provided comprising an SSID 15 having at least one imaging array disposed on a distal end 16 thereof and a first optical element 20 disposed on the distal end 16 of the SSID 15. The first optical element 20 has a distal end 21 and a proximal end 22 defining a first longitudinal length. A GRIN lens 25 is disposed on the distal end 21 of the first optical element 20 and a second optical element 30 is disposed on the distal end 26 of the GRIN lens 25 defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end 22 of the first optical element 20.

In one aspect of the invention, a light source exterior to the first and second optical elements 20, 30 and the GRIN lens 25 is provided. The light source may be capable of propagating light at a predetermined wavelength. One example of an exterior light source is a fiber optic cable 35 disposed along a longitudinal length of the microscope 10. The fiber optic cable 35 may be coupled to a light source capable of modulating the frequency of the wavelength propagated through the cable. As shown in FIG. 3a, the fiber optic cable 35 may deliver a beam of light at a specific wavelength to the distal end 11 of the microscope 10. In one aspect of the invention, light from the fiber optic cable 35 reflects off the surface of an object in contact with the distal end 31 of the second optical element 30 and is conveyed through the microscope and onto the surface of the SSID 15. In yet another aspect, near infrared light, for example, from the fiber optical cable 35 is propagated into the object, reflected off subsurface portions of the object, and thereafter conveyed through the microscope 10.

In another aspect of the invention, an outer surface of the first optical element 20, the GRIN lens 25, and at least a portion the second optical element 30 are coated with an opaque material. The opaque material reduces problems that may result if incident light enters the microscope 10.

Figure 4:
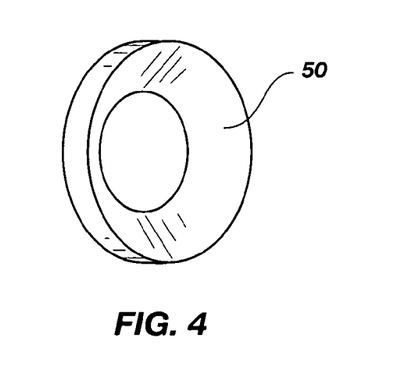
FIG. 4 is a perspective view of an annular prism in accordance with one embodiment of the present invention.

In one embodiment, a light collimation device, such as a parabolic mirror, is disposed on a distal end of the second optical element 30. In another aspect, the device further comprises a light reflection device disposed on a distal end of the second optical element 30. One example of a light reflection device is an annular prism 50 as illustrated in FIGS. 3b and 4.

In one embodiment of the present invention, the first optical element 20 and/or the second optical element 30 comprise a transparent cylinder. The transparent cylinder may comprise, for example, a solid silica-based material. In an additional example, the transparent cylinder may comprise a fluid-filled cylinder wherein the fluid has an index of refraction in the range of approximately 1 to 2.

In another embodiment of the present invention, the first optical element 20 and the second optical element 30 are longitudinally adjustable. In one aspect, the first optical element 20 and second optical element 30 comprise a volume of air. In yet another aspect, the first optical element 20 and the second optical element 30 comprise a fluid. In one embodiment, the fluid has an index of refraction less than 1.1.

According to one embodiment of the present invention, the first optical element 20 is adjusted by moving the SSID 15 closer to the GRIN lens 25. This may be accomplished by disposing a portion of the SSID 15 in a track member 19, such as a journaled track member. The track member 19 is oriented along a longitudinal length of the microscope 10 and comprises a means for moving the SSID within the track member. In a similar manner, the second optical element 30 may be adjusted by moving the distal end 31 of the second optical element 30 closer to the GRIN lens 25.

Figure 5:
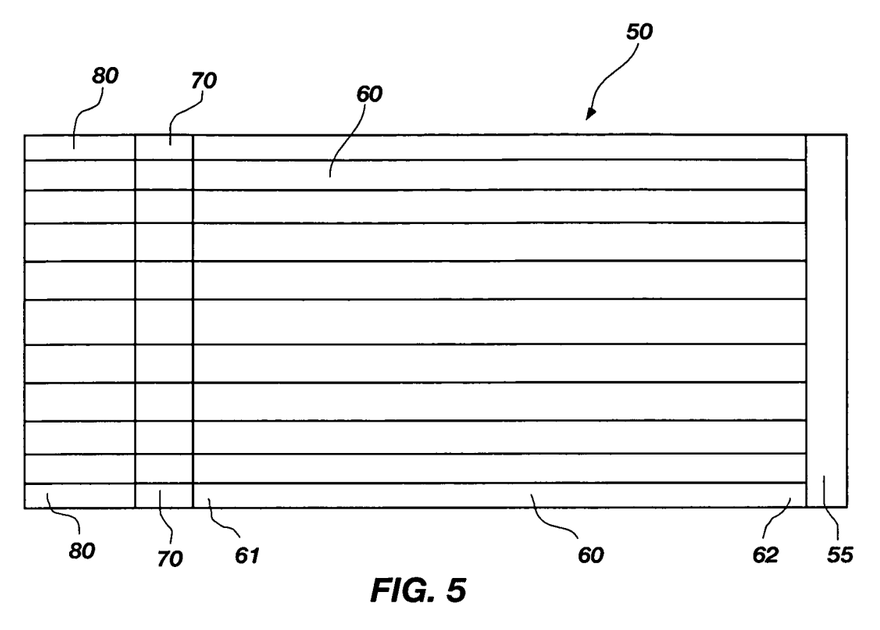
FIG. 5 is a side view of a SSID microscope in accordance with one embodiment of the present invention.
Figure 6:
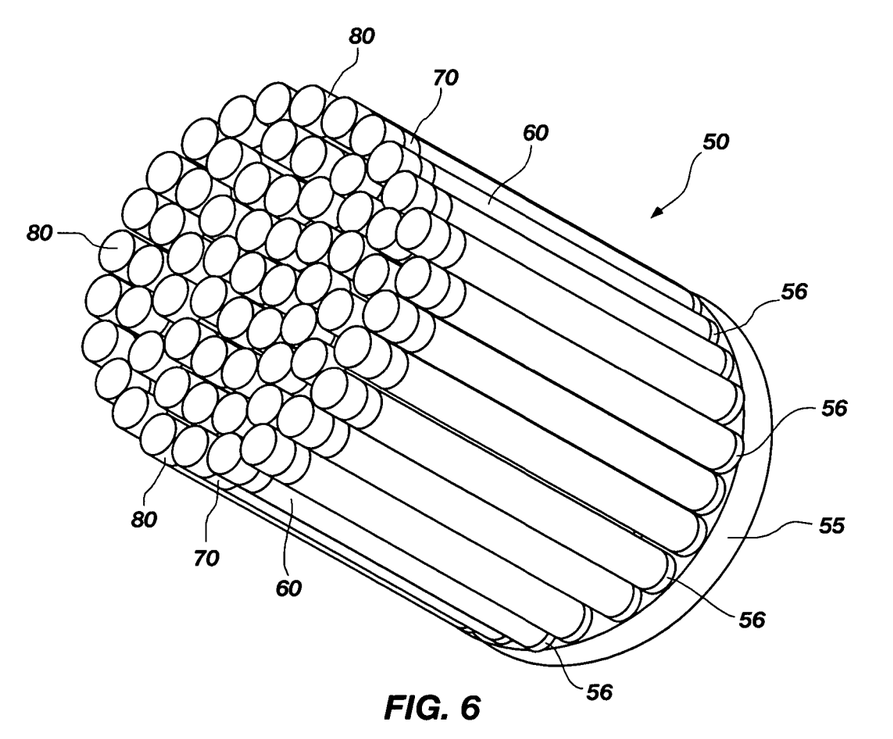
FIG. 6 is a perspective view of the SSID microscope of FIG. 5.

Referring now to FIGS. 5 and 6, in yet another embodiment of the present invention, the microscope 50 comprises an SSID 55 with a plurality of imaging arrays 56 disposed thereon. Each imaging array has a single image magnification system disposed thereon. Each image magnification system comprises a first optical element 60 disposed on a distal end of the imaging array having a distal end 61 and a proximal end 62 defining a first longitudinal length. The image magnification system further comprises a GRIN lens 70 disposed on the distal end 61 of the first optical element 60. A second optical element 80 is disposed on the distal end of the GRIN lens 70 defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end 62 of the first optical element 60.

In addition to the forgoing examples, a method of magnifying an object is contemplated herein. Referring generally to FIGS. 1a, 1b, 2, 3a, and 3b, in one exemplary embodiment, the method comprises providing a device having an SSID 15 and first and second optical elements 20, 30 with a GRIN lens 30 disposed between the first and second optical elements 20, 30. The ratio of the longitudinal length of the first optical element 20 to the second optical element 30 is maintained such that when viewing the object at a predetermined wavelength of light, the object is magnified at a predetermined level of magnification and the focal plane of the magnified object is aligned at the proximal end 22 of the first optical element 20. The method further comprises orienting the device such that the object which one wishes to magnify is disposed adjacent the distal end 31 of the second optical element 30. In one aspect, the object is in direct contact with the distal end 31 of the second optical element 30. A predetermined wavelength of light is propagated onto the surface of the object and a portion of the propagated light is reflected off the surface of the object and onto the SSID 15.

In an additional embodiment, the method comprises propagating a predetermined wavelength of light (e.g., near infra red) into a portion of the object in addition to or in lieu of propagating a predetermined wavelength of light onto the surface of the object. The light that is reflected off of the surface and/or from inside the object is then received by the SSID 15. The method further comprises generating a signal in response to the light received by the SSID 15 and transmitting said signal to a signal processor and image display device (not shown).

In an additional embodiment, the method further comprises adjusting the longitudinal length of the first optical element 20 and the second optical element 30 to vary the magnification of the object. The method further comprises adjusting the wavelength of light propagated onto and/or into the object in order to properly align the focal plane on the face of the SSID 15. Advantageously, a user, such as a medical practitioner may advance the microscope 10 into a portion of a patient, and conduct a detailed in-vivo examination of the patient's tissues. By adjusting the lengths of the first optical element 20 and/or the second optical element 30, the medical practitioner can vary the magnification of a single object. Further, by varying the wavelength of the light propagated into and/or onto the object, numerous characteristics of the tissue may be observed.

Figure 7:
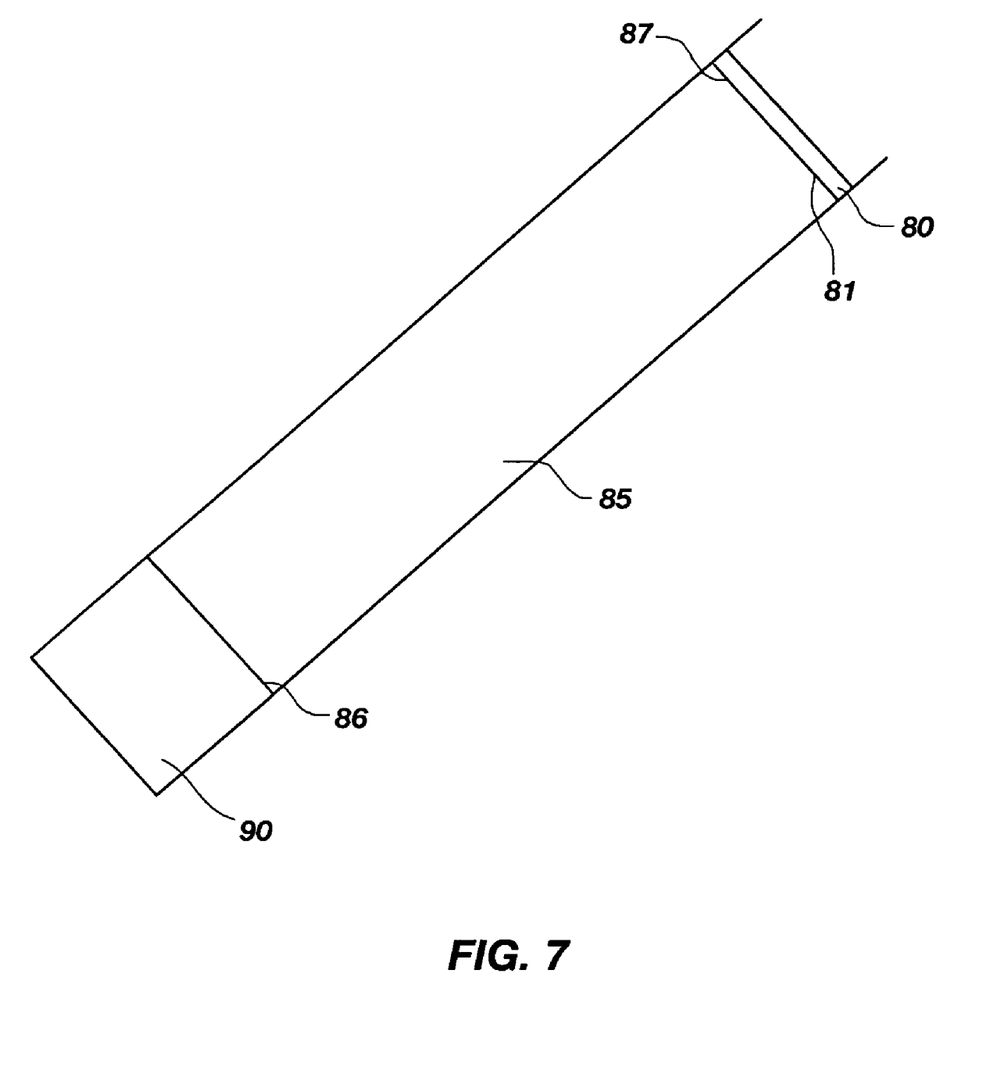
FIG. 7 is a side view of a SSID microscope in accordance with one embodiment of the present invention.

In additional embodiment of the present invention, a device for magnifying an object is disclosed comprising an SSID 80 having at least one imaging array disposed on a distal end thereof. A first optical element 85 is disposed on the distal end 81 of the SSID, the first optical element 85 having a distal end 86 and a proximal end 87 defining a first longitudinal length. A second optical element 90 is disposed on the distal end 86 of the first optical element 85 defining a second longitudinal length. The first longitudinal length and the second longitudinal length are configured such that when viewing the object at a predetermined wavelength of light, the object is magnified at a predetermined level of magnification and the focal plane of the magnified object is aligned at the proximal end of the first optical element. In one aspect of the present invention, the first optical element 85 is a GRIN lens. In yet another aspect of the invention, the second optical element 90 is a GRIN lens.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A device for magnifying an object, comprising:
an SSID having at least one imaging array disposed on a distal end thereof;
a first optical element disposed on the imaging array, the first optical element having a first end and a second end defining a first longitudinal length;
a GRIN lens having a first end and a second end, the first end of the GRIN lens being disposed on the second end of the first optical element; and
a second optical element having a first end and a second end, the first end of the second optical element being disposed on the second end of the GRIN lens and defining a second longitudinal length;

wherein the first longitudinal length and the second longitudinal length are configured such that when viewing the object at a predetermined wavelength of light, the object is magnified at a predetermined level of magnification and the focal plane of the magnified object is aligned at the first end of the first optical element.

2. The device of claim 1, further comprising a light source exterior to the first and second optical elements and the GRIN lens, capable of propagating light at a predetermined wavelength.

3. The device of claim 1, further comprising a light reflection device disposed on the second optical element.

4. The device of claim 3, wherein the light reflection device is an annular prism.

5. The device of claim 1, wherein the first and second optical elements comprise a material having an index of refraction less than 1.1.

6. An SSID microscope, comprising:
   an SSID having at least one imaging array disposed thereon;
   a longitudinally adjustable first optical element having a first end and a second end defining a longitudinal length, the first end of the first optical element being disposed on the imaging array;
   a GRIN lens having a first end and a second end, the first end of the GRIN lens being disposed on the second end of the first optical element; and
   a longitudinally adjustable second optical element disposed on the second end of the GRIN lens;
   wherein the ratio of the longitudinal length of the first optical element to the longitudinal length of the second optical element is maintained such that when viewing the object at a predetermined wavelength of light, the object is magnified at a predetermined level of magnification and the focal plane of the magnified object is aligned at the first end of the first optical element.

7. The microscope of claim 6, wherein the first and second optical elements comprise an adjustable volume of fluid.

8. The microscope of claim 6, wherein the first and second optical elements comprise a material having an index of refraction less than 1.1.

9. The microscope of claim 6, further comprising a light source configured to propagate light at a predetermined wavelength of light.

10. The microscope of claim 6, wherein the SSID is disposed within a journaled track member configured to allow the position of the SSID to be adjustable with respect to the longitudinally adjustable first optical element.

11. The microscope of claim 6, wherein the GRIN lens is disposed within a journaled track member configured to allow the position of the GRIN lens to be adjustable with respect to the longitudinally adjustable second optical element.

12. A device for magnifying an object within a cavity, comprising
   an elongate member having at least one light source disposed therein, said light source configured to propagate light near the distal end of the elongate member at a predetermined wavelength of light;
   an SSID having at least one imaging array disposed on a distal end of the elongate member, said SSID operably connected to a signal processor;
   a first optical element disposed on a distal end of the SSID, the first optical element having a first end and a second end defining a first longitudinal length;
   a GRIN lens having a first end and a second end, the first end of the GRIN lens disposed on the second end of the first optical element; and
   a second optical element having a first end and a second end defining a second longitudinal length, the first end of the second optical element being disposed on the second end of the GRIN lens;
   wherein the first longitudinal length and the second longitudinal length are configured such that when viewing the object at a predetermined wavelength of light, the object is magnified at a predetermined level of magnification and the focal plane of the magnified object is aligned at the first end of the first optical element.

13. The device of claim 12, wherein the first and second optical elements comprise a material having an index of refraction less than 1.1.

14. The device of claim 12, further comprising a light reflection device disposed on a distal end of the second optical element.

15. The device of claim 14, wherein the light reflection device is an annular prism.

* * * * *